United States Patent [19]

Platz

[11] Patent Number: 4,652,759
[45] Date of Patent: Mar. 24, 1987

[54] COUNTERBALANCED RADIATION DETECTION SYSTEM

[75] Inventor: Winfried Platz, Southington, Conn.

[73] Assignee: Siemens Gammasonics, Inc., Des Plaines, Ill.

[21] Appl. No.: 630,903

[22] Filed: Jul. 13, 1984

[51] Int. Cl.⁴ .............................................. G01T 1/20
[52] U.S. Cl. .................................................. 250/363 S
[58] Field of Search ... 250/363.2, 363.3, 363.4, 363.5 250/363.8, 366; 378/167, 174, 189

[56] References Cited

U.S. PATENT DOCUMENTS 3,870,886  3/1975  Casale ........................... 250/363 SF
3,983,399  9/1976  Cox, Jr. et al. ............... 250/363 SF
4,057,727  11/1977  Muehllehner et al. ....... 250/363 SA Primary Examiner—Janice A. Howell
Attorney, Agent, or Firm—Mark H. Jay

[57] ABSTRACT

A counterbalanced radiation detection system is provided which comprises a stand and a first and second radiation detectors tiltably connected with the stand. A torque transforming means is connected between the first and second radiation detectors for transforming the torque created by one of the radiation detectors opposite to the torque created by the other radiation detector.

15 Claims, 4 Drawing Figures

COUNTERBALANCED RADIATION DETECTION SYSTEM

BACKGROUND OF THE INVENTION

1. Field of the Invention

The invention relates to a counterbalanced radiation detection system. In particular, the invention relates to a rotational counterbalanced gamma camera system.

2. Description of the Prior Art

The brochure "ROTA CAMERA A versatile gamma camera system for SPECT and conventional imaging" of Siemens Gammasonics, Inc., 2000 Nuclear Drive, Des Plaines, Ill. 60018, No. MG/5700-006-121B INT 4M 11/82 illustrates a rotational counterbalanced gamma camera system. The system comprises a base and a gantry connected with the base. It further comprises a first and second gamma camera heads which are both tiltably connected with the gantry. During rotating of the gantry both camera heads describe an orbit about a patient under investigation. The tilting angle of each camera head is a measure for the radius of the orbit. Each gamma camera head is counterbalanced by a separate counterweight, such as of lead.

U.S. Pat. No. 4,057,727 (Muehllehner et al.) describes a position imaging system having a gantry and two camera heads which are positioned on opposite sides of the circumference of the gantry. During rotation of the gantry one camera head always counterbalances the other one while both camera heads are rotating on an orbit about a patient. However, the camera heads are not tiltable.

U.S. Pat. No. 3,797,819 (Platz et al.) depicts a supporting table for patients comprising a table plate and a lever mechanism for positioning the table plate in different heights.

SUMMARY OF THE INVENTION

1. Objects

It is an object of this invention to provide a counterbalanced radiation detection system having two radiation detectors which counterbalance each other and which are tiltable.

It is another object of this invention to provide a counterbalanced gamma camera system having two gamma camera heads which counterbalance each other and which are tiltable.

It is still another object of this invention to provide a rotational counterbalanced gamma camera system having two gamma camera heads which counterbalance each other and which are tiltable.

2. Summary

According to this invention an improved counterbalanced radiation detection system is provided, which comprises:
(a) a stand;
(b) a first radiation detection tiltably connected with the stand;
(c) a second radiation detector tiltably connected with the stand; and
(d) a torque transforming means connected between the first and second radiation detectors for transforming the torque created by one of the radiation detectors opposite to the torque created by the other radiation detector.

The torque transforming means according to this invention counterbalance the tiltable first and second radiation detectors against each other. No additional counterweight for each radiation detector is necessary.

Also according to this invention a counterbalanced gamma camera system is provided, which comprises:
(a) a stand;
(b) a first gamma camera head tiltably connected with the stand;
(c) a second gamma camera head tiltably connected with the stand; and
(d) a torque transforming means connected between the first and second gamma camera head for transforming the torque created by one of the gamma camera heads opposite to the torque created by the other gamma camera head.

Furthermore, according to this invention a rotational counterbalanced camera system is provided, which comprises:
(a) a stand having a rotatable gantry;
(b) means for rotating the gantry;
(c) a first gamma camera head tiltably connected with the gantry;
(d) a second gamma camera head tiltably connected with the gantry; and
(e) a torque transforming means connected between the first and second gamma camera head for transforming the torque created by one of the gamma camera heads opposite to the torque created by the other gamma camera head.

The foregoing and other objects, features and advantages of the invention will be apparent from the following more particular description of a preferred embodiment of the invention, as illustrated in the accompanying drawings.

DETAILED DESCRIPTION OF THE PREFERRED EMBODIMENT

Figure 1:
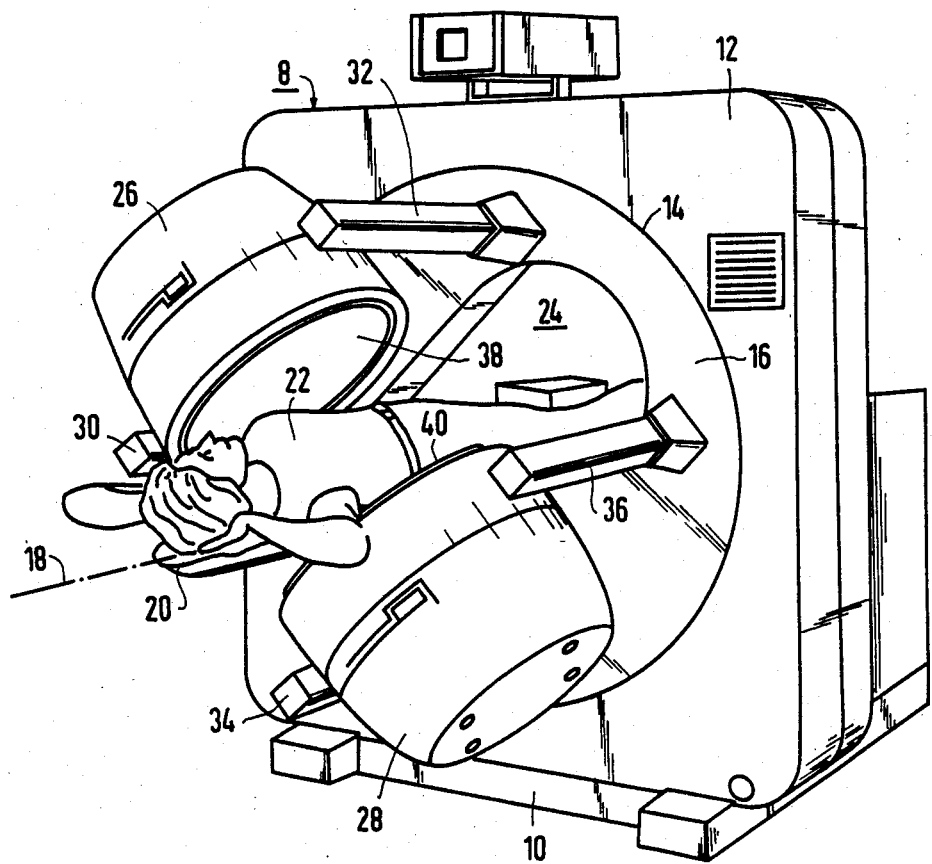
FIG. 1 is an overview of a rotational counterbalanced gamma camera system according to this invention.

The rotational counterbalanced gamma camera system of FIG. 1 comprises a stand 8 having a base 10 and a gantry 12 mounted vertically on the base 10. The central opening 14 of the gantry 12 contains a ring structure 16 which is rotatable about a horizontal axis 18. A table top 20 for carrying a patient 22 extends along the horizontal axis 18 through the central opening 24 of the ring structure 16. A first and second gamma camera heads 26 and 28 are accommodated on the ring structure 16 by means of first, second, third and fourth cantilevers 30, 32, 34 and 36, respectively.

The camera heads 26 and 28 are preferably ZLC camera heads. In SPECT (single photon emission computed tomography) applications, the dual camera heads 26 and 28 double the sensitivity of the system and thus improve image statistics for a given counting rate. Alternatively, they can be used in conventional procedures. For SPECT reconstructive imaging, the camera heads 26 and 28 are jointly rotated around the patient 22. The camera heads 26 and 28 track the center line of rotation precisely as they are rotated around the patient 22. Accurate information regarding the positions of the camera heads are continuously transmitted for imaging reconstruction.

The first and second gamma camera heads 26, 28 each comprise a first and second collimators 38 and 40, respectively.

Figure 2:
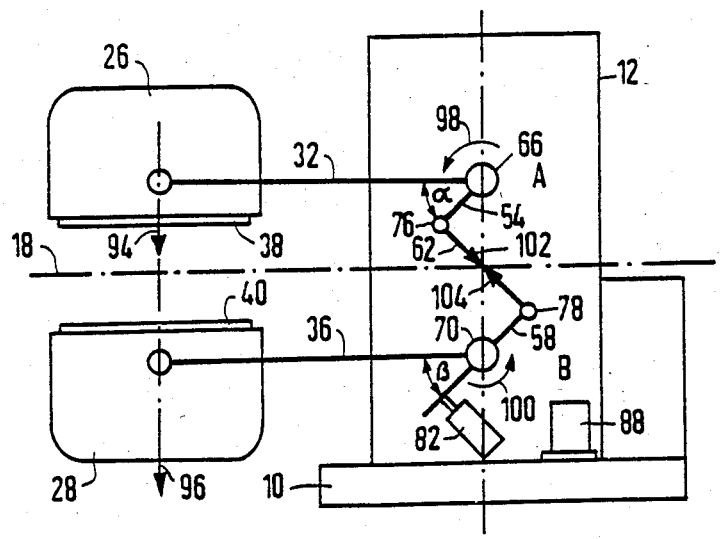
FIG. 2 is a side view of a system according to FIG. 1 showing in a schematic diagram a torque transforming mechanism for the first and second camera heads.
Figure 3:
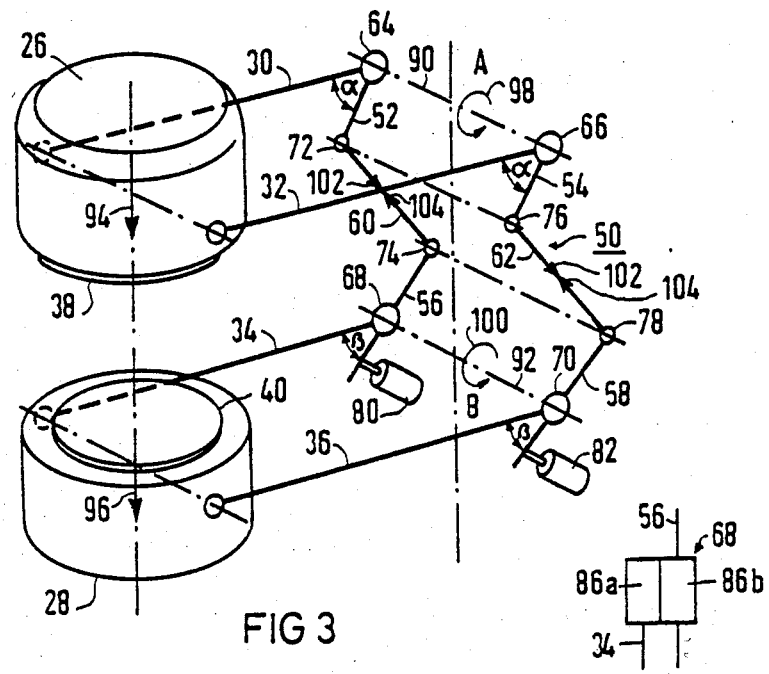
FIG. 3 is the torque transforming mechanism of FIG. 2 in a perspective view.

As illustrated in FIGS. 2 and 3 the rotational counterbalanced gamma camera system according to FIG. 1 comprises a torque transforming mechanism 50 which is connected between the first, second, third and fourth cantilevers 30, 32, 34 and 36, for transforming the torque created by one of the gamma camera heads opposite to the torque created by the other gamma camera head.

In FIGS. 2 and 3 the torque transforming mechanism 50 includes a rod mechanism. The rod mechanism comprises a first rod mechanism portion containing a first rod 52 and a second rod 54. The rod mechanism also has a second rod mechanism portion including a third rod 56 and a fourth rod 58. Finally, the rod mechanism contains a third rod mechanism portion which comprises a fifth rod 60 and a sixth rod 62.

The first, second, third and fourth cantilevers 30, 32, 34, 36 are tiltably mounted in the interior of the ring structure 16 of the gantry 12 by means of a first, second, third and fourth trunnions 64, 66, 68 and 70.

The first rod 52 is connected with the first cantilever 30 by means of the first trunnion 64 under a first angle $\alpha$. Correspondingly, the second rod 54 is connected with the second cantilever 32 by means of the second trunnion 66 under the first angle $\alpha$.

The third rod 56 is connected with the third cantilever 34 via the third trunnion 68 under a second angle $\beta$. Correspondingly, the fourth rod 58 is connected with the fourth cantilever 36 via the fourth trunnion 70 under the second angle $\beta$.

The rod mechanism also comprises a fifth, sixth, seventh and eighth trunnions 72, 74, 76 and 78. The fifth rod 60 is connected at one end with the first rod 52 by means of the fifth trunnion 72 and at its other end with the third rod 56 by means of the sixth trunnion 74 as illustrated in FIG. 3. Correspondingly, the sixth rod 62 is connected at its one end with the second rod 54 by means of the seventh trunnion 76 and at its other end with the fourth rod 58 by means of the eighth trunnion 78, as illustrated in FIGS. 2 and 3.

In FIGS. 2 and 3 the first angles $\alpha$ equal the second angles $\beta$.

Figure 4:
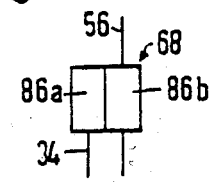
FIG. 4 is a more detailed structure of a trunnion of the torque transforming mechanism.

A first and second motor drives 80, 82 allow for varying the second angles $\beta$, thereby also automatically varying the first angles $\alpha$. This enables positioning of both gamma camera heads 26, 28 at different distances to the horizontal rotational axis 18 of the gantry 12 at the same time. As illustrated in FIG. 4 with respect to trunnion 68 for angle variation each of the trunnions 68 and 70 comprises a first and second trunnion portions 84 and 86 which are normally locked with each other, however, which can stepwisely be rotated with respect to each other only for the purpose of angle variation by means of motor drives 80, 82.

Rotation of the ring structure 16 of the gantry 12 is performed by a rotational motor drive, generally designated with 88 in FIG. 2. Oval orbiting with both gamma camera heads 26, 28 can be achieved by motorizing (not shown) the tilting axis 90 through the first and second trunnions 64, 66. The other tilting axis 92 follows accordingly.

According to this invention the torque transforming mechanism 50 transforms the torque created by one gamma camera head opposite to the torque created by the other gamma camera head.

For example, as illustrated in FIGS. 2 and 3 the weights of the first and second gamma camera heads 26, 28 pull the heads in the directions of arrows 94, 96. The results are the torques A and B, as indicated by arrows 98, 100. However, torque A created by the first gamma camera head 26 which is counterlockwise, is transformed into a clockwise torque created by the second gamma camera head 28 by means of the torque transforming mechanism 50.

This situation, which is illustratred in FIGS. 2 and 3 by oppositely directed arrows 102 and 104, has as a result that in each tilting position both gamma camera heads 26, 28 counterbalance each other via the torque transforming mechanism 50.

Additional counterweights are not necessary. The system also remains balanced if collimators 38, 40 of the gamma camera heads 26, 28 are changed to different types with different weights.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims apended hereto.

What is claimed is:

1. A counterbalanced radiation detection system, comprising:
    (a) a stand;
    (b) a first radiation detector;
    (c) a first radiation detector arm means for tiltably connecting the first radiation detector with the stand;
    (d) a second radiation detector;
    (e) a second radiation detector arm means for tiltably connecting the second radiation detector with the stand, whereby the tilting angles of said radiation detector arm means define a distance between said radiation detectors; and
    (f) a torque transforming means connected between the first and second radiation detector arm means for transforming the torque created by one of the radiation detectors in a sense opposed to the torque created by the other radiation detector.

2. The system according to claim 1, wherein each of said radiation detectors is a gamma camera head.

3. The system according to claim 1, wherein the torque transforming means comprises a rod means connected between the first and second radiation detector arm means for transforming a counterclockwise directed torque created by one of the radiation detectors into a clockwise directed torque created by the other radiation detector.

4. The system according to claim 3, wherein the rod means comprising:
    (a) a first rod means portion connected with the first radiation detector arm means under a first angle;
    (b) a second rod means portion connected with the second radiation detector arm means under a second angle; and
    (c) a third rod means portion tiltably connected between the first and second rod means portions.

5. The system according to claim 4, wherein
(a) the first radiation detector arm means is tiltably connected with the stand by means of a first trunnion means;
(b) the second radiation detector arm means is tiltably connected with the stand by means of a second trunnion means;
(c) the first rod means portion is connected with the first radiation detector arm means via the first trunnion means; and
(d) the second rod means portion is connected with the second radiation detector arm means via the second trunnion means.

6. The system according to claim 4, wherein the third rod means portion has a first and second ends and is connected at the first end with the first rod means portion by means of a third trunnion means and at the second end with the second rod means portion by means of a fourth trunnion means.

7. The system according to claim 4, wherein
(a) the first radiation detector arm means comprises a first and second cantilevers for carrying the first radiation detector therebetween;
(b) the second radiation detector arm means comprises a third and fourth cantilevers for carrying the second radiation detector therebetween;
(c) the first rod means portion comprises a first rod connected with the first cantilever under the first angle and a second rod connected with the second cantilever under the first angle;
(d) the second rod means portion comprises a third rod connected with the third cantilever under the second angle and a fourth rod connected with the fourth cantilever under the second angle; and
(e) the third rod means portion comprises a fifth rod tiltably connected between the first and third rods and a sixth rod tiltably connected between the second and fourth rods.

8. The system according to claim 7, wherein
(a) the first, second, third and fourth cantilevers are tiltably connected with the stand by means of a first, second, third and fourth trunnions, respectively; and
(b) the first, second, third and fourth rods are connected with the first, second, third and fourth cantilevers via the first, second, third and fourth trunnions, respectively.

9. The system according to claim 7, wherein the fifth and sixth rods each have a first and second ends and wherein the fifth rod is connected at its first end with the first rod by means of a fifth trunnion and at its second end with the third rod by means of a sixth trunnion and wherein the sixth rod is connected at its first end with the second rod by means of a seventh trunnion and at its second end with the fourth rod by means of an eighth trunnion.

10. The system according to claim 4, further comprising means connected with the rod means for varying the first and second angles.

11. The system according to claim 10, wherein the angle varying means comprising means for varying only one of the first and second angles, thereby automatically varying the other angle.

12. The system according to claim 1, wherein the stand comprises a base and a gantry mounted on the base for rotating the first and second radiation detectors around a rotational axis.

13. The system according to claim 12, wherein each of said radiation detectors is a gamma camera head.

14. A counterbalanced gamma camera system, comprising:
(a) a stand;
(b) a first gamma camera head tiltably connected with the stand;
(c) a second gamma camera head tiltably connected with the stand; and
(d) a torque transforming means connected between the first and second gamma camera head for transforming the torque created by one of the gamma camera heads opposite to the torque created by the other gamma camera head.

15. A rotational counterbalanced gamma camera system, comprising:
(a) a stand having a rotatable gantry;
(b) means for rotating the gantry;
(c) a first gamma camera head tiltably connected with the gantry;
(d) a second gamma camera head tiltably connected with the gantry; and
(e) a torque transforming means connected between the first and second gamma camera head for transforming the torque created by one of the gamma camera heads opposite to the torque created by the other gamma camera head.

* * * * *